United States Patent
Kawashima et al.

(10) Patent No.: US 6,960,670 B2
(45) Date of Patent: Nov. 1, 2005

(54) METHOD FOR PRODUCTION OF MALEIC ANHYDRIDE

(75) Inventors: Tadayoshi Kawashima, Himeji (JP); Yoshitake Ishii, Himeji (JP); Kei Hamamoto, Himeji (JP); Souichi Yamada, Himeji (JP); Tetsuya Kajihara, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 9 days.

(21) Appl. No.: 10/174,669

(22) Filed: Jun. 19, 2002

(65) Prior Publication Data

US 2003/0023101 A1 Jan. 30, 2003

(30) Foreign Application Priority Data

Jun. 19, 2001 (JP) .................................. 2001-185340
Sep. 28, 2001 (JP) .................................. 2001-302013

(51) Int. Cl.[7] .......................................... C07D 307/60
(52) U.S. Cl. ...................................... 549/262; 549/257
(58) Field of Search .................................. 549/262, 257

(56) References Cited

U.S. PATENT DOCUMENTS 2,729,600 A * 1/1956 Beach et al. ................ 549/262
3,357,994 A * 12/1967 Popp et al. ................. 549/262

FOREIGN PATENT DOCUMENTS

| FR | 1317308 | 12/1961 |
|---|---|---|
| JP | 41003172 | 2/1966 |
| JP | 50050316 | 6/1975 |
| JP | 03076311 | 2/1986 |
| JP | 63313782 | 12/1988 |
| JP | 05261292 | 10/1993 |
| JP | 05262754 | 10/1993 |
| JP | 05262755 | 10/1993 |
| JP | 06145160 | 5/1994 |

OTHER PUBLICATIONS

Handbook of Chemistry & Physics (43rd Edition) Chemical Rubber Publ. Co., Cleveland, Ohio (1961) p. 944–945.*

* cited by examiner

*Primary Examiner*—Bernard Dentz
(74) *Attorney, Agent, or Firm*—McCarter & English, LLP

(57) ABSTRACT

This invention discloses a method for producing maleic anhydride comprising an azeotropic distillation step to dehydrate a crude maleic acid-containing aqueous solution, which method is characterized by as an azeotropic solvent (1) using an organic solvent exhibiting a maximum dissolving concentration of the organic solvent in water in the range of 0.1–5% by weight at a temperature of 20° C. According to this invention, it is made possible to prevent the occurrence of a blocking substance, allow a continuous operation for a long time, and remove by-produced acid components by a process of distillation for azeotropic dehydration.

2 Claims, 1 Drawing Sheet

METHOD FOR PRODUCTION OF MALEIC ANHYDRIDE

BACKGROUND OF THE INVENTION

1. Field of the Invention

This invention relates to a method for the production of maleic anhydride which comprises a step for the azeotropic dehydration of a crude maleic acid containing aqueous solution, and more particularly to a method for the production of maleic anhydride, characterized by azeotropic dehydration by using an organic solvent having the maximum concentration in water in the range of 0.1–5% by weight at a temperature of 20° C.

2. Description of Related Arts

The maleic anhydride is a general-purpose compound which is possessed of a double bond of large reactivity and two carboxyl groups in the form of an anhydride and, therefore, is capable of chemically performing various reactions and is extensively used in various fields covering plasticizers and agricultural pesticides as well as pharmaceutical preparations, polyester resins, and alkyd resins. This maleic anhydride is produced by a method which comprises oxidizing such an aliphatic hydrocarbon as n-butane which has not less than four carbon atoms or benzene in a reactor for catalytic gas phase oxidation, recovering maleic acid from the produced gas containing maleic anhydride and maleic acid, and refining the recovered maleic anhydride. A water which obtained by washing the waste gas discharged during the production of phthalic anhydride by the reaction of catalytic gas phase oxidation of naphthalene or o-xylene contains maleic acid in an appreciable quantity. The maleic anhydride, therefore, is produced by a method which comprises recovering the water and changing maleic acid to maleic anhydride.

Generally, when maleic anhydride is produced via the reaction of catalytic gas phase oxidation, the method which directly subjects the maleic anhydride obtained by the reaction of catalytic gas phase oxidation in its unmodified form to purification and which absorbs the obtained maleic anhydride once in an aqueous solution and purifies the aqueous solution containing the crude maleic acid, subsequently converts maleic acid into maleic anhydride are available, for example.

JP-B-41-3172, for example, discloses as a means to produce maleic anhydride by subjecting a mixed gas of benzene and air to catalytic gas phase oxidation, a method for continuous production of maleic anhydride which comprises exposing a reaction gas containing maleic anhydride to water thereby obtaining a crude maleic acid containing aqueous solution, dissolving the aqueous solution in fused maleic anhydride, and continuously adding the resultant mixed solution into a mixed solution of maleic anhydride and aromatic hydrocarbon at a temperature in the range of 130–160° C. thereby effecting liquid-phase dehydration of maleic acid. The aromatic hydrocarbons used for the purpose of dehydrating maleic anhydride include xylene, cymen, ethyl benzene, diethyl benzene, and dichlorobenzene, for example. The quantity of the aromatic hydrocarbon used for this purpose varies with the kind of the azeotropic solvent to be used. Generally, it is 2–5 times the quantity of the water which is formed in consequence of the dehydration of maleic acid.

JP-A-50-50316 discloses a method for obtaining maleic anhydride by absorbing in water a maleic acid-containing gas resulting from the catalytic oxidation of an aliphatic or aromatic hydrocarbon thereby forming a crude maleic acid-containing aqueous solution, treating the aqueous solution at a temperature in the range of 100–150° C. under a pressure in the range of 400–760 mmHg thereby deriving fused maleic acid, and subjecting the fused maleic acid to distillation for dehydration at a temperature in the range of 115–165° C. under a pressure in the range of 40–200 mmHg. This method is characterized by converting part of maleic acid into maleic anhydride, treating the impurities consequently entrained with water thereby forming a solid phase composed of fumaric acid and other insoluble impurities and an aqueous liquid phase containing maleic acid, expelling the solid phase from the system by filtration, and recirculating the aqueous filtrate of maleic acid for purification. This method is directed to precluding the method for continuous production of maleic anhydride from inducing faults such as gradual deposition of impurities on the inner walls of devices, blockage of such devices due to the deposition, and degradation of the conduction of heat.

Further, JP-A-63-313782 discloses a method for the production of maleic anhydride which is directed, while the washings of waste gas containing organic substances comprising maleic acid as a main component at a concentration in the range of 20–40% by weight is azeotropically distilled with o-xylene in a dehydrating column to convert the maleic acid into maleic anhydride and obtain maleic anhydride, to removing with a vacuum evaporator the pitch entrained by the maleic anhydride withdrawn from the dehydrating column through the lower part thereof.

When maleic anhydride is obtained by the reaction of catalytic gas phase oxidation, however, the apparatus for continuous production frequently suffers the interior thereof to incur blockage with such impurities as benzoquinone which is by-produced in the reaction and with fumaric acid which is by-produced in the process for purification of maleic anhydride, for example. While JP-A-50-50316 mentioned above teaches a method for precluding such a method for continuous production of maleic anhydride from inducing faults such as gradual deposition of impurities on the inner walls of devices, blockage of such devices due to the deposition, and degradation of the conduction of heat, the method has not been capable of preventing the blockage fully satisfactorily. The method disclosed by JP-A-41-3172 falls short of satisfaction.

As a means to repress the occurrence of this blockage chemically unlike the methods described above, JP-B-03-76311 discloses a method for the production of maleic anhydride which is directed, during the production of maleic anhydride as from a crude maleic acid-containing aqueous solution obtained by absorbing in water the reactive gas resulting from the reaction of catalytic gas phase oxidation of benzene and a $C_4$ hydrocarbon fraction, toward concentrating and dehydrating the crudemaleic acid-containing aqueous solution by the addition of an aqueous hydrogen peroxide solution. According to this patent publication, the crude maleic acid-containing aqueous solution contains various kinds of impurities and these impurities are suffered to occur in the form of a mixture of intermediate products and by-products without reference to the kind of hydrocarbon to be used as a raw material and are not perfectly prevented easily even by such means as modification of a reaction catalyst. It offers an explanation purporting that the cause for the persistence of these impurities is ascribable to the promotion of resinification or gelation by the cooperation of a phenol and an aldehyde or a quinone and an aldehyde, for example, and that the apparatus is consequently blocked. It is held that the formation of a resinous or gel-like substance can be prevented by adding hydrogen peroxide to the crude maleic acid-containing aqueous solution. This prevention, however, entails a new problem that the apparatus for purification is corroded by the formic acid which is inevitably by-produced. Further, the hydrogen peroxide is known as a polymerization initiator for maleic anhydride. The azeotropic distillation for dehydration which has a particularly high working temperature, therefore, newly forms a maleic acid polymer which is destined to serve as a blocking substance.

This invention, in view of the problems mentioned above, contemplates providing such a method for the production of maleic anhydride as allows a protracted continuous operation for the process of purification which is capable of preventing the generation of a blocking substance without inducing relevant devices to corrode, preventing the deposition of a blocking substance in a column for azeotropic dehydration and distillation which, because of a complicated internal structure, renders the work of washing the interior of the column irksome and difficult, and removing the impurities by-produced in the reaction.

SUMMARY OF THE INVENTION

The present inventors, as a result of pursuing a detailed study on the identification of substances by-produced in the reaction of catalytic gas phase oxidation, the blocking substance generated in the process for production of maleic anhydride, and particularly the blocking substance occurring in the column for azeotropic dehydration, have been ascertained that the blockage is generated by the adhesion of a plurality of insoluble substances such as the condensate of an aldehyde with a quinone by-produced in the reaction of catalytic gas phase oxidation, the homopolymer of maleic acid, and the precipitates of fumaric acid, i.e. an isomer of maleic acid, and maleic acid to the interiors of such purifying devices as a column for azeotropic dehydration. They have also discovered that since maleic acid and fumaric acid have higher degrees of solubility in water than organic solvents, they alleviate the state of oil-water separation in a distilling column operated to effect azeotropic dehydration by using a hydrophilic organic solvent and prevent the blockage in the process of dehydration with unusually high efficiency. This invention has been perfected based on the knowledge. They have further found that such as hydrophilic organic solvents are effective in preventing the blockage avoid forming an azeotropic composition with light boiling acid components by-produced in the reaction, particularly formic acid and acetic acid, and manifest only a weak effect in expelling them by distillation and attaining the expected purification and that the removal of formic acid and acetic acid can be accomplished by additionally using such an organic solvent as forms an azeotropic composition with formic acid and acetic acid. This invention has been perfected as a result.

This invention is directed to providing a method for producing maleic anhydride comprising an azeotropic distillation step to dehydrite a crude maleic acid-containing aqueous solution, by using an organic solvent as an azeotropic solvent (1), which method is characterized by, which organic solvent exhibits a maximum dissolving concentration of the organic solvent in water in the range of 0.1–5% by weight at a temperature of 20° C. Maleic acid and fumaric acid which have heretofore posed the problem of arising as a precipitate during the step of concentration and dehydration in the production of maleic anhydride have high degrees of solubility in water and generally low degrees of solubility in organic solvents. This invention, by using such an organic solvent of ketone or ester as possesses compatibility with water and also possesses specific properties, eliminates the state of oil-water separation in a distilling column for azeotropic dehydration and represses the reaction of condensation without concentrating aldehydes and quinones, the substances for causing the formation of a condensate, into the water phase as an azeotropic solvent (1). It is also made possible to increase the solubility of the precipitate in the azeotropic mixture of maleic acid, fumaric acid, and maleic anhydride polymer and prevent the blockage with a precipitate.

Further, this invention is directed toward a method for producing maleic anhydride comprising an azeotropic distillation step to dehydrite a crude maleic acid-containing aqueous solution by azeotropic distillation, which method is characterized by using as an azeotropic solvent a mixture of an azeotropic solvent (1) forming an azeotropic composition with water and exhibiting a maximum dissolving concentration in water in the range of 0.1–5% by weight at a temperature of 20° C. and an azeotropic solvent (2) forming an azeotropic composition with formic acid and/or acetic acid. Since the organic solvent of the ketone or the ester mentioned above to be used as an azeotropic solvent (1) avoids forming an azeotropic composition with by-produced acids, particularly formic acid and acetic acid, and renders the separation of such by-produced acid difficult, it forms a cause for lowering the purity of the refined maleic anhydride. The system produced by mixing at a specific ratio an azeotropic solvent possessing affinity for water and an azeotropic solvent possessing the property of forming an azeotropic composition with acids, particularly formic acid and acetic acid, can materialize a refining process which is capable of preventing the precipitate from blocking the column for azeotropic dehydration and meanwhile expelling the by-produced acids at the stage of the distillation for azeotropic dehydration.

DESCRIPTION OF THE PREFERRED EMBODIMENTS

Figure 1:
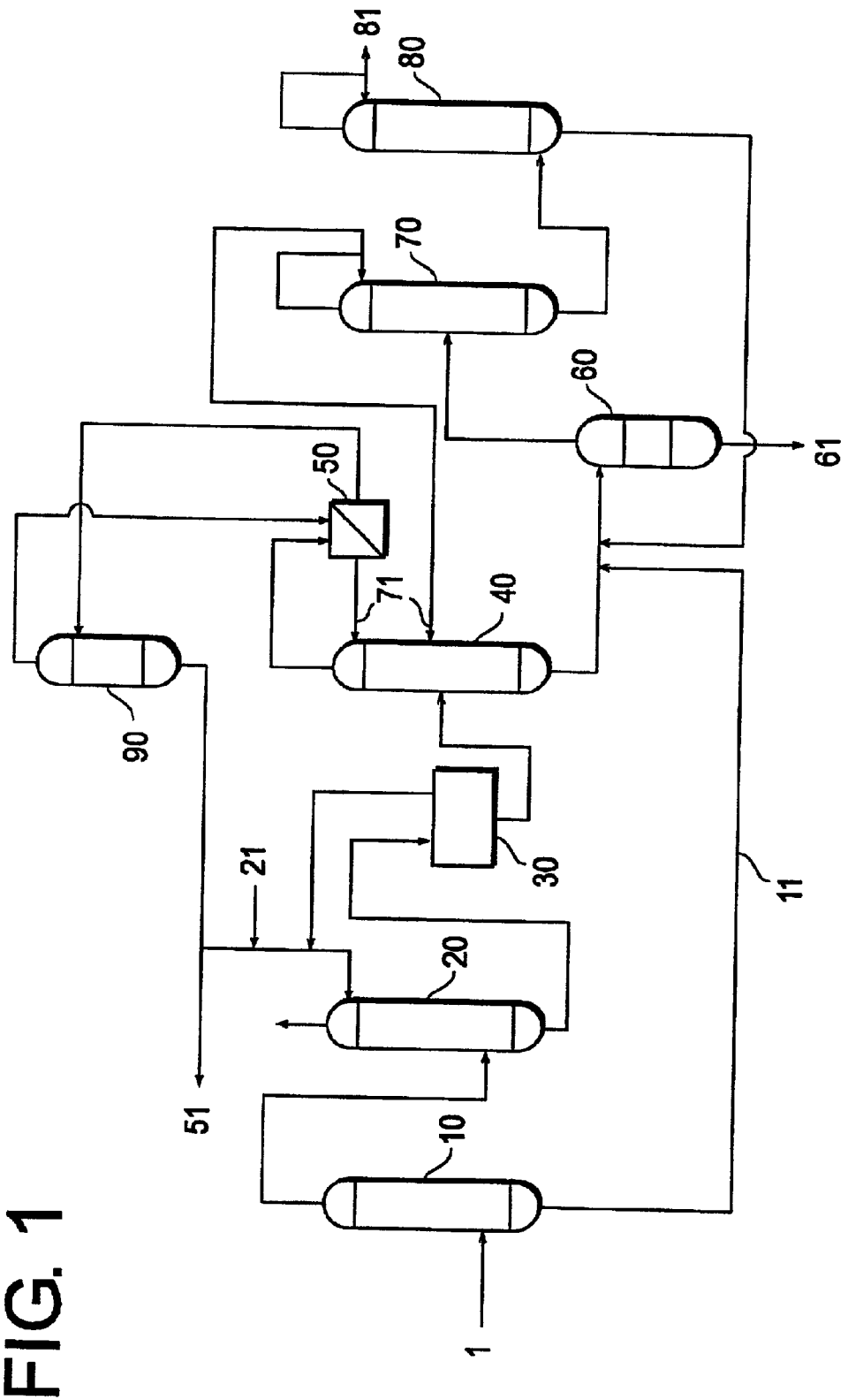
FIG. 1 is a process diagram depicting a preferred embodiment of the method for the production of maleic anhydride according to this invention.

The first aspect of this invention concerns a method for producing maleic anhydride comprising an azeotropic distillation step to dehydrate a crude maleic acid-containing aqueous solution, which method is characterized by as an azeotropic solvent (1) using an organic solvent exhibiting a maximum dissolving concentration in water in the range of 0.1–5% by weight at a temperature of 20° C., that is, a method for producing maleic anhydride comprising an azeotropic distillation step to dehydrate a crude maleic acid-containing aqueous solution by using an organic solvent as an aceotripic solvent (1), wherein said organic solvent exhibits a maximum dissolving concentration in water in the range of 0.1–5% by weight at a temperature of 20° C. A ketone or an ester answers the description of the azeotropic solvent (1) mentioned above. Since this azeotropic solvent alleviates the state of oil-water separation which occurs between water and the azeotropic mixture during the distillation for azeotropic dehydration and forms a homogeneous phase or a state closely approximating it, it allows production of maleic anhydride which entrains a solid precipitate only sparingly. The term "maximum dissolving concentration" as used in the present specification is defined in the section of working examples.

In azeotropically dehydrating a crude maleic acid-containing aqueous solution, the practice of using an azeotropic solvent generally prevails. The distillation for azeotropic dehydration has been heretofore performed by using an organic solvent, i.e. such an aromatic compound as xylene, cymen, ethyl benzene, diethyl benzene, or dichlorobenzene, which has a comparatively low degree of solubility in water. When an organic solvent having a low degree of solubility in water is used, since it is devoid of miscibility with water and maleic acid even at the internal temperature of the distilling column, the water contained in the crude maleic acid-containing aqueous solution and the azeotropic solvent assume the state of oil-water separation in the distilling column. The maleic acid contained in the crude maleic acid-containing aqueous solution and the aldehyde and the quinone which are impurities are soluble in water and exist mainly in the water phase. They are, therefore, concentrated in the water phase and the condensation reaction of the aldehyde and the quinone is liable to proceed therein. The accelerated condensation reaction forms one cause for yielding a solid precipitate. Since maleic acid and fumaric acid which is an isomer thereof and maleic anhydride polymer are soluble in water and exhibit substantially no solubility in organic solvents, they tend to be precipitated in organic solvents and this fact likewise forms one cause for blockage. The present inventors' detailed visual observation of the operating condition in the distilling column for azeotropic dehydration has revealed that, in the region of the interior of the column which yields to dehydration insufficiently and allows the presence of hydraulic pressure, the aldehyde and the quinone tend to be concentrated and the condensate tends to induce blockage on the water phase side and, in the region of the column interior which promotes dehydration till the water content nearly ceases to exist, the precipitation of maleic acid and maleic anhydride polymer which are soluble in water tend to induce the blockage.

It has been revealed that when the azeotropic dehydration is performed by using an organic solvent which possesses hydrophilicity, the state of oil-water separation in the distilling column is alleviated, the localization of the aldehyde and the quinone in the water phase is repressed, the concentration of these compounds in the water phase is lowered, and the condensation reaction between the two compounds is controlled. The organic solvent possessing such hydrophilicity is required to exhibit no reactivity with maleic acid, fumaric acid, the condensate liable to form, and the maleic acid polymer, and to exhibit a maximum dissolving concentration of the organic solvent in water in the range of 0.1–5% by weight, preferably in the range of 0.5–4% by weight, and particularly preferably in the range of 1–3% by weight, at a temperature of 20° C. If the maximum dissolving concentration in water falls short of 0.1% by weight, the shortage will tend to induce the state of oil-water separation mentioned above. Conversely, if it exceeds 5% by weight, the excess which indeed brings an effect in improving the state of oil-water separation nevertheless will be at a disadvantage in suffering the loss of the organic solvent in the water phase to increase and consequently decreasing the quantity of the organic solvent to be separated and recovered.

The azeotropic solvent (1) to be used in this invention is required to exhibit a maximum dissolving concentration of maleic acid in azeotropic solvent (1) in the range of 0.1–10.0% by weight, preferably 0.1–8.0% by weight, and particularly preferably 0.3–7.0% by weight, more particularly preferably 1.0–7.0% by weight, at a temperature of 20° C. (under normal pressure). When the azeotropic solvent (1) mentioned above to be used in this invention has high solubility in maleic acid and affinity for maleic acid as well, the precipitation of maleic acid and fumaric acid during the process of azeotropic dehydration can be prevented and, as a result, the precipitation of such a water-soluble solid as maleic anhydride polymer can be also prevented. The use of this organic solvent (1) constitutes one preferred embodiment of this invention because it can simultaneously prevent the isomerization to fumaric acid and the precipitation of fumaric acid.

The azeotropic solvent (1) to be used in this invention is required to have a boiling point in the range of 80–190° C., preferably in the range of 100–170° C., and particularly preferably in the range of 110–160° C. under a pressure of 1013 hPa. If the boiling point exceeds 190° C., the excess will be at a disadvantage in suffering this boiling point to approximate closely to the boiling point of maleic anhydride and the ratio of the maleic anhydride to be expelled by distillation together with the organic solvent to heighten. Conversely, if this boiling point falls short of 80° C., the shortage will prevent the production from proceeding advantageously because the temperature of the reaction of dehydration in the distilling column is lowered and the speed of dehydration is lowered as well.

As concrete examples of the azeotropic solvent (1) for use in this invention, ketones such as methyl isobutyl ketone, diisopropyl ketone, 3-pentanone, 2-hexanone, 3-hexanone, and 2-heptanone, esters such as amyl acetate and allyl acetate, and alcohols such as methyl cyclohexanol and 2-ethyl-1-hexnol may be cited. This invention particularly finds such ketones as methyl isobutyl ketone, diisopropyl ketone, and 2-hexanone and such esters as allyl acetate preferable as an azeotropic solvent (1) because these ketones and esters possess solubility in water, exalt the degrees of solubility of maleic acid, fumaric acid, and maleic acid polymer in the azeotropic solvent (1), and allow solution of the problem of precipitation. Incidentally, the maximum dissolving concentration in this invention is presumed to represent the magnitude that is found under the normal pressure (1013 hPa), though variable with the pressure. The maximum dissolving concentration of the azeotropic solvent (1) which is used in this invention may be expressed as follows based on the data inserted in "Chemical Handbook" (Maruzen Co., Ltd.) and Beilstein Online (search by STN International). Specifically, methylisobutyl ketone (1.91% by weight), diisopropyl ketone (0.43% by weight), 3-pentanone (4.6% by weight), 2-hexanone (1.75% by weight), 3-hexnaone (1.57% by weight), 2-heptanone (0.44% by weight), amyl acetate (0.25% by weight), allyl acetate (2.8% by weight), and 2-ethyl-1-hexnol (0.10% by weight) are found from the data. Ketones prove particularly advantageous in respect that they excel in solubility in maleic acid. This is because the ketones satisfy the conditions mentioned above, excel in the effect of preventing the occurrence of a blocking substance during the process for the production of maleic anhydride and in the solubility of a blocking substance, and possess no reactivity with maleic acid and maleic anhydride.

The azeotropic solvent (1) mentioned above is such that when it is used as an aqueous solution of azeotropic solvent in the production of maleic anhydride by the catalytic gas phase oxidation of benzene as a raw material, it is particularly effective in the prescribed process under discussion because the quantities of aldehydes and quinones, the substances responsible for the condensate which is one of the blocking substances in the column for azeotropic dehydration, are large. These aldehydes and quinones, however, occur when benzene is used as a raw material, when maleic anhydride is recovered from the gas generating in the production of maleic anhydride by using such aliphatic hydrocarbon as n-butane as a raw material, and when maleic anhydride is recovered from the waste gas generating in the production of maleic anhydride by using naphthalene or o-xylene as a raw material. Thus, the method contemplated by this invention is useful in the method of production using any of the raw materials mentioned above. It is effective, for example, when the method incorporates a step which comprises absorbing by washing with water a maleic anhydride-containing gas obtained by the reaction of catalytic gas phase oxidation of n-butane and subjecting the gas to the distillation for azeotropic dehydration using an organic solvent possessing the characteristic properties mentioned above. It manifests an effect in preventing the column for azeotropic dehydration against blockage and enables the column to be operated for a long time.

This invention, in the azeotropic dehydration of the crude maleic acid-containing aqueous solution, can use the azeotropic solvents (1) mentioned above either singly or in the form of a combination of two or more members.

Further, even when an organic solvent devoid of the solid state properties of the azeotropic solvent (1) is present in a mixed state, the same effect as is found when the azeotropic solvent (1) mentioned above is used may be possibly obtained on the condition that the resultant solvent mixture possesses properties equivalent to those manifested by the azeotropic solvent (1), namely the temperature of azeotrope with water in a specific range, the solubility of maleic acid, and the solubility in water. This invention, even when it uses the azeotropic solvent (1) either by itself or in combination with another solvent, is capable of preventing the occurrence of a condensate of an aldehyde and a quinone and preventing the precipitation of such solid substances as maleic acid, fumaric acid, and maleic acid polymer so long as the solvent mixture exhibits as characteristic properties the temperature of azeotrope with water in the range of 70–100° C., preferably in the range of 80–100° C., and particularly preferably in the range of 85–100° C., under a fixed pressure of 1013 hPa, the maximum dissolving cencentration of maleic acid in the azeotropic solvent mixture in the range of 0.1–10.0% by weight, preferably 0.1–8.0% by weight, and particularly preferably 0.3–7.0% by weight, more particularly preferably 1.0–7.0% by weight at a temperature of 20° C., and the maximum dissolving concentration in water in the range of 0.1–5% by weight, preferably in the range of 0.5–4% by weight, and particularly preferably in the range of 1–3% by weight at a temperature of 20° C.

A composition which is formed of methyl isobutyl ketone, 3-pentanone, or 3-hexanone as the azeotropic solvent (1) and other organic solvent than the azeotropic solvent (1) used in respective quantities such as to total 100% by weight, which other organic solvent accounts for a proportion in the range of 1–40% by weight, preferably in the range of 3–35% by weight, and particularly preferably in the range of 5–30% by weight. If the organic solvent having a low degree of solubility in water, namely the other organic solvent than the azeotropic solvent (1), is used in a quantity exceeding 40% by weight, the excess will possibly lower the effect of repressing the precipitation. If it is used in a quantity falling short of 1% by weight, the other azeotropic solvent incorporated at all will fail to bring the expected effect. Incidentally, by using the organic solvents having low degrees of solubility in water in a mixed state, it is made possible to decrease the quantity of the azeotropic solvent (1) to be used and permit economic selection of organic solvents. Such other organic solvent has the advantage of offering freedom of choice from among various organic solvents on the sole condition that it avoid hindering the azeotropic dehydration of the aforementioned crude maleic acid-containing aqueous solution. As concrete examples of the other organic solvent which is used advantageously, hydrocarbons such as toluene, xylene, octane, cumen, mesitylene, ethyl benzene and dimethyleyclohexan, and sulfonates such as isopropyl sulfide and allyl sulfide, and halogenides such as bromobenzene and iodopropane may be cited. If the maximum dissolving concentration of maleic acid in the solvent mixture exceeds the range, the excess will be at a disadvantage in suffering the recovery of maleic acid to decrease by the high solubility at azeotropic dehydration, if the maximum dissolving concentration is falls short of the range, the shortage will be at a disadvantage in suffering maleic acid and/or fumaric acid to be educed in the solvent mixture.

Further, the solvent mixture mentioned above, as occasion demands, may not contain the azeotropic solvent (1) mentioned above at all. This invention, as described above, is characterized by originating in the discovery that by using an azeotropic solvent possessing specific hydrophilicity, it is made possible to alleviate the state of oil-water separation mentioned above in the distillation of azeotropic dehydration, repress the reaction of condensation of an aldehyde and a quinone, and prevent the occurrence of a blocking substance. What fulfils this object does not need to be limited to the azeotropic solvent that is possessed of the characteristic properties mentioned above. That is, the present invention in a method for producing maleic anhydride which comprises a step for dehydrating a crude maleic acid-containing aqueous solution by azeotropic distillation, without reference to the kind of a solvent to be used, can accomplish the azeotropic dehydration by using a solvent mixture exhibiting a point of azeotropy with water in the range of 70–100° C. under a pressure of 1013 hPa, a maximum dissolving concentration of maleic acid in the solvent mixture in the range of 0.1–10.0% by weight, preferably 0.1–8.0% by weight, particularly preferably 0.3–7.0% by weight, more particularly preferably 1.0–7.0% by weight at a temperature of 20° C., and a maximum dissolving concentration of the azeotropic solvent (1) in water in the range of 0.1–5% by weight at a temperature of 20° C. The solvent mixture of amyl alcohol and amyl acetate is a typical example of the solvent mixture of such a composition. When this solvent mixture is composed of 45.9% by weight of water, 12.2% by weight of amyl alcohol, and 41.9% by weight of amyl acetate, for example, the point of azeotropy with water is 94.9° C., the maximum dissolving concentration of maleic acid at a temperature of 20° C. in the mixed solvent formed of 12.2 parts by weight of amyl alcohol and 41.9 parts by weight of amyl acetate is 6.68% by weight, and the maximum dissolving concentration in water at a temperature of 20° C. is 0.19% by weight. By using this solvent mixture, it is made possible to prevent the deposition of a blocking substance in a distilling column for azeotropic dehydration which requires a complicated and difficult cleaning work when the blockage occurs at all owing to the complicated internal structure of the distilling column and to enable the distilling column to be operated for a long time.

The quantity of the azeotropic solvent (1) or the solvent mixture to be used in the process for azeoropic dehydration is preferred to be in the range of 0.5–10 parts by weight, particularly in the range of 2–5 parts by weight, based on the total of the quantity of the water contained in the crude maleic acid-containing aqueous solution and the quantity of the water generated in consequence of the anhydridization taken as one part by weight, though variable with the ratio of the components forming the azeotropic solvent (1) or the solvent mixture to be used. The fact that the quantity of the organic solvent to be used relative to water is small brings a commercial advantage of decreasing the quantity of heat to be spent.

Now, one preferred embodiment of the method for production of maleic anhydride according to the first aspect of this invention will be described below with reference to FIG. 1. In the diagram of FIG. 1, 1 denotes a reaction gas, 10 a maleic anhydride collecting device, 11 a crude maleic anhydride, 20 a water-washing absorbing column, 21 a recycling absorbent, 30 a concentrating device, 40 a column for azeotropic dehydration, 50 an oil-water separating tank, 51 a waste water, 60 a high-boiling separting column, 61 a residue, 70 a solvent separation column, 71 an azeotropic solvent, 80 a purifying column, 61 a purified maleic anhydride, and 90 a solvent recovering column.

First, the raw material gas is supplied to a reactor for catalytic gas phase oxidation not shown in the diagram. The raw material gas thus supplied does not need to be particularly restricted but has only to be capable of generating maleic acid as the product of the reaction of the catalytic gas phase oxidation. Any known hydrocarbon to be used for producing maleic anhydride can be used as the raw material for the supply. As concrete examples of the raw material for the supply, hydrocarbons of not less than four carbon atoms such as benzene, butane, (n-butane), butenes (1-butene and 2-butene), and butadienes (1,3-butadiene), and o-xylene and naphthalene may be cited. These raw materials may be used either singly or in the form of a combination of two or more members. This invention prefers benzene in the other raw materials mentioned above as the raw material for the reaction of catalytic gas phase oxidation. The by-product of the reaction varies with the kind of the raw material to be used. The reason for this choice of benzene is that the blocking substance, particularly the condensate, which is generated by the by-product occurring in the use of benzene as a raw material is effectively attained.

As respects the catalyst to be used in the reactor, a known catalyst can be used on the condition that it is capable of forming maleic acid or maleic anhydride. The oxidizing catalyst which contains vanadium as an active component, for example, can be used. As concrete examples of the catalyst which can be used advantageously, the catalysts which are disclosed in JP-A-05-261292, JP-A-05-262754, JP-A-05-262755, and JP-A-06-145160 may be cited.

The reaction for catalytic gas phase oxidation is literally a reaction of oxidation. Thus, a molecular oxygen-containing gas is supplied together with the raw material gas. As the molecular oxygen-containing gas, though air is generally used, the air diluted with an inert gas and the air enriched with added oxygen are also usable.

As regards the reaction conditions, those used in any of the methods heretofore known to the art may be adopted. They may be properly altered, depending on the kind of the oxidizing catalyst to be used, the concentration of the raw material to be supplied, and the concentration of the molecular oxygenic-containing gas, for example. The reaction is carried out at a temperature in the range of 300–600° C. by using a vanadium-phosphorus catalyst, for example. The reaction gas which is discharged from the reactor for catalytic gas phase oxidation entrains the reaction components by-produced along with maleic anhydride and the impurities contained in the raw material gas in their unaltered form and entrains the low-boiling substances and high-boiling substances which are the oxides of the impurities mentioned above and the raw material compound and the uncondensable gas as well. Incidentally, the term "low-boiling substances" as used in the present specification refers to such substances as possess lower boiling points thanmeleic acid in the standard state. As concrete examples of the low-boiling substances, formic acid, acetic acid, acrylic acid, formaldehyde, acegtaldehyde, p-benzoquinone, and water may be cited. Then, the term "high-boiling substances" refer to such substances as possess higher boiling points than maleic acid in the standard state. As concrete examples of these substances, phthalic anhydride and fumaric acid may be cited. The term "uncondensable gas" refers to such a substance as assumes a gaseous form in the standard state. As concrete examples of the uncondensable gas, nitrogen, oxygen, air, propylene, propane, carbon monoxide, and carbon dioxide may be cited. The term "standard state" mentioned above refers to the state which exists under normal pressure of 1013 hPa (one atmosphere) at a temperature of 0° C.

The reaction gas which is obtained by the reaction of catalytic gas phase oxidation of benzene is generally composed of 2–5% by weight of maleic anhydride (hereinafter, the term "maleic anhydride" in the composition of the reaction gas will be construed as containing maleic acid as reduced to maleic anhydride), 0.01–0.1% by weight of low-boiling substances excluding steam, i.e. acetic acid and aldehyde, 0.005–0.03% by weight of high-boiling substances such as phthalic anhydride, and the balance of the uncondensable gas and steam.

Then, the reaction gas discharged from the reactor is supplied to the maleic anhydride collecting device (10). In the maleic anhydride collecting device (10), the reaction gas is cooled at a temperature exceeding the melting point of maleic anhydride and not exceeding the boiling point thereof, namely at a temperature preferably in the range of 55–120° C. and particularly preferably in the range of 60–100° C. and part of the maleic anhydride is collected in the liquid state. Owing to the persistence of the residual pressure of the vapor of maleic anhydride, the maleic anhydride exists in a large quantity in the reaction gas after the cooling. Subsequently to the step for collecting maleic anhydride by the cooling performed as described above, therefore, the waste gas arising after this step is supplied to the water-washing absorbing column (20) to collect the maleic anhydride existing copiously in an aqueous solution and recover a crude maleic acid-containing aqueous solution.

As regards the operating conditions for the water-washing absorbing column (20), those used in any of the methods heretofore known to the art may be adopted. Though water can be used as an absorbent, the water or the aqueous solution which is generated during the step for concentrating and dehydrating maleic acid may be used as part of the absorbent. The top of the column prefers a low temperature for the purpose of exalting the ratio of absorption of maleic anhydride. The temperature of the top of the absorbing column, therefore, is kept by using a cooling device annexed to the water-washing absorbing column (20) preferably in the range of 10–90° C., and more preferably in the range of 20–60° C. If this temperature falls short of 10° C., the shortage will be at a disadvantage in lowering the maximum dissolving concentration of maleic acid to the extent of inducing precipitation of crystals, degrading the shelf efficiency of the absorbing column (20) owing to the increase in the pressure loss of the water-washing absorbing column (20) and the deterioration of the dispersibility of liquid, and moreover necessitating an excess cooling energy. Conversely, if the temperature exceeds 90° C., the excess will induce the ratio of collection of maleic acid to decrease.

In the water-washing absorbing column (20) which has admitted the reaction gas, the absorbent (21) is introduced into the interior of the absorbing column through the upper part of the column and brought into counter flow contact with the maleic anhydride-containing gas and made to absorb maleic anhydride so that the maleic acid concentration in the bottom liquid of the column may fall in the range of 10–80% by weight, preferably in the range of 20–60% by weight. If the concentration of maleic acid exceeds 80% by weight, the excess will be at a disadvantage in requiring the temperature of absorption to be raised to not lower than 90° C. for the purpose of precluding precipitation of maleic acid and suffering the ratio of absorption to fall. Conversely, if the concentration falls short of 10% by weight, the shortage will be at a disadvantage in suffering the water distilled at the step of concentrating and dehydrating the crude maleic acid-containing aqueous solution to increase to the extent of rendering the operation uneconomical.

Instead of carrying out the collection of the maleic anhydride in the liquid state by the use of the maleic anhydride collecting device (10) as illustrated in FIG. 1, the reaction gas may be wholly supplied to the water-washing absorbing column (20) and collected in the form of a crude maleic acid-containing aqueous solution.

Subsequently, the crude maleic acid-containing aqueous solution is supplied to the column for azeotropic dehydration (40). In this case, the crude maleic acid-containing aqueous solution is effective and advantageous since the fact that the crude maleic acid-containing aqueous solution results from absorbing with water the reaction gas formed by the catalytic gas phase oxidation of benzene implies excellence of the effect of preventing blockage and that the aqueous solution is effective in removing at the same step such low-boiling substances as formic acid, acetic acid, acrylic acid, formaldehyd, acetaldehyde, and p-benzoquinone which are contained therein. Incidentally, the crude maleic acid-containing aqueous solution may be distilled so as to expel water and induce concentration before it is supplied to the column for azeotropic dehydration (40). As the concentrating device (30) which fits the concentration herein, a thin-film evaporator can be used besides such heretofore known columns as a plate column, a wetted-wall column, and a spray column. The concentrating device is preferred to be the thin-film evaporator.

As concrete examples of the column for azeotropic dehydration (40) which can be used herein, such known columns as a plate column, a packed column, a wetted-wall column, and a spray column may be cited. This column for azeotropic dehydration (40) is generally preferred to be a plate column or a packed column similarly to the water-washing absorbing column (20) mentioned above. It is meanwhile advantageous to use a distilling column having a number of theoretical plates of not less than 3, preferably falling in the range of 4–40, and particularly preferably in the range of 5–15. If this the number of theoretical plates falls short of 3, the shortage will be at a disadvantage in allowing only an insufficient time for the contact between maleic acid and an azeotropic solvent and inducing a decline in the ratio of dehydration and increasing the distillation of maleic anhydride to the top of the column and consequently aggravating the loss of maleic anhydride. The number of theoretical plates has only to suffice to the extent of avoiding such adverse influences as mentioned above. If the number of steps is unduly large, the excess will raise the cost of equipment and prove uneconomical.

This invention is characterized by using as the azeotropic solvent (1) in the dehydration of a crude maleic acid-containing aqueous solution an organic solvent exhibiting a maximum dissolving concentration in water at least in the range of 0.1–5% by weight at a temperature of 20° C. The various organic solvents cited previously are concrete examples of the azeotropic solvent (1) under discussion here. It is particularly preferable to use MIBK. The conditions for the azeotropic dehydration vary with the kind of azeotropic solvent to be used. When MIBK, for example, is used as the azeotropic solvent, 3–5 parts by weight of the MIBK is supplied to the column for azeotropic dehydration (40) per part by weight of the crude maleic acid-containing aqueous solution. Generally, the pressure at the top of the column (absolute pressure) is set in the range of 100–2000 hPa and preferably in the range of 300–1500 hPa. If the pressure falls short of 100 hPa, the shortage will not only enlarge the vacuum device but also lower the inner temperature of the column and will induce crystallization of maleic acid and fumaric acid possibly to the extent of disabling the distillation. Conversely, if this pressure exceeds 2000 hPa, the excess will not only heighten the temperature of the bottom of the column so as to require an addition to the size of the boiler and encourage the generation of a polymer but also induce the necessity for rendering the relevant equipment proof against pressure at the cost of economy. Then, the temperature of the top of the column is in the range of 50–150° C., preferably in the range of 60–130° C. If this temperature falls short of 50° C., the shortage will result in enlarging a cooling device. Conversely, if the temperature exceeds 150° C., the excess will not only dispose the interior of the column to induce polymerization of maleic acid readily but also increase the distillation of maleic anhydride to the top of the column and consequently aggravate the loss of the maleic anhydride.

The temperature of the bottom of the column is in the range of 130–200° C., preferably in the range of 150–195° C. If this temperature falls short of 130° C., the shortage will retard the reaction for dehydration of maleic acid, render the dehydration of maleic acid insufficient, and eventually induce a decline in the yield of maleic anhydride. Conversely, if the temperature exceeds 200° C., the excess will be at a disadvantage in suffering this temperature to approximate closely to the boiling point of maleic anhydride and rendering easy the occurrence of decomposition and polymerization. For the purpose of materializing this azeotropic dehydration, it suffices to adjust such factors as the kind and the quantity of addition of an azeotropic solvent, the concentration of water in the crude maleic acid-containing aqueous solution, the change of steps for supply of the raw material, the reflux ratio of the cooling device annexed to the top of the column, the number of plates in the column, the temperature, the pressure, and others.

As the azeotropic solvent or the solvent mixture to be used in the azeotropic dehydration, the azeotropic solvent (71) which is recovered at the step for producing maleic anhydride may be reused. The azeotropic solvent does not need to be directly supplied to the column for azeotropic dehydration (40) as illustrated in FIG. 1 but may be supplied into the column for azeotropic dehydration (40) as mixed with the raw material being supplied. Further, as the azeotropic solvent, the solvent mixture which possesses the properties described in this invention may be used. This solvent mixture is a solvent mixture possessing a point of azeotropy with water in the range of 70–100° C. under a pressure of 1013 hPa and is preferred to exhibit the maximum dissolving concentration of maleic acid in the solvent mixture in the range of 0.1–10.0% by weight at a temperature of 20° C. and the maximum dissolving concentration in water in the range of 0.1–5% by weight at a temperature of 20° C. It suffices to supply a mixture of solvents so adjusted as to possess such properties as mentioned above to the column of azeotropic dehydration (40).

In this invention, the oil-water separating column (50) is annexed to the top of the column for azeotropic dehydration (4) to reflux the azeotropic solvent of the distillate from the top of the column during the course of the azeotropic dehydration. Since the organic solvent which is used in this invention is characterized by possessing solubility in water, the water phase side of the distillate from the top of the column contains an organic solvent. For the purpose of establishing a more economical process, it is advantageous to recover this organic solvent into the distilling column for azeotropic dehydration and put it to use. The water phase of the distillate from the top of the column, when supplied to the solvent recovering column (90), is enabled to expel through distillation the organic solvent dissolved therein, separate it through the top of the column, forward it to the oil-water separating column (50), recover it as the azeotropic solvent in the distilling column for azeotropic dehydration and put it to use. From the bottom of the column, the recovered water which contains no organic solvent is obtained. Incidentally, as the solvent recovering column (90), a plate column, a packed column, a wetted-wall column, and a spray column which have been known to the art are usable.

The method which comprises supplying the bottom liquid of the column for azeotropic dehydration (40) to the high-boiling separating column (60), separating the high boiling substances from the liquid, and thereafter subjecting the residue to the subsequent step of purification proves advantageous since it can prevent the apparatus from being blocked. Phthalic anhydride, fumaric acid, and high-boiling polymer and condensate which are by-produced by the reaction of catalytic gas phase oxidation, for example, are discharged as the residue (61).

The high-boiling separating column (60) to be used herein may be in the continuous mode or the batch wise mode. Besides such heretofore known columns as a plate column, a packed column, a wetted-wall column, and a spray column, a rotary retaining column type evaporator and a thin-film evaporator canbe advantageously used. The devices of the modes mentioned above may be used either singly or in the form of a combination of two or more members arranged in series or parallelly. When the operation is performed in the continuous mode, thin-film evaporators arranged in a series pattern in two rows are used advantageously. Incidentally, the crude maleic anhydride (11) may be supplied together with the bottom liquid of the column for azeotropic dehydration (40) to the high-boiling separating column (60) and purified therein.

As regards the conditions for distillation in the high-boiling separating column (60), the distillation using a distilling column can be carried out under the conditions heretofore known to the art. The pressure in the top of the column (absolute pressure), for example, is in the range of 1–40 kPa, preferably in the range of 3–20 kPa. The temperature in the top of the column is kept in the range of 70–170° C., preferably in the range of 90–140° C., during the course of the operation of the column. The quantity of the distillate may be properly decided, depending on the tolerance of the high-boiling impurities in the product. The reflux ratio is generally in the range of 0.3–3.

When the thin-film evaporator is used as the high-boiling separating column (60), the temperature is generally set in the range of 80–200° C., preferably in the range of 110–180° C.

When the gas component discharged from the high-boiling separating column suffers persistence of the azeotropic solvent besides the maleic anhydride, it is supplied subsequently to the solvent separating column (70) and stripped of the azeotropic solvent therein. This step may be omitted when the distillation for azeotropic dehydration is performed under such conditions that the azeotropic solvent leaves no residue or only a trace of residue behind in the bottom.

As this solvent separating column (70), such known columns as a plate column, a packed column, a wetted-wall column, and a spray column are usable. The solvent separating column (70) is generally preferred to be a plate column or a packed column similarly to the water-washing absorbing column (20) mentioned above.

As the conditions for the operation of the azeotropic solvent separating column, the conditions heretofore known to the art may be adopted. The temperature of the top of the column is in the range of 60–140° C., the ref lux ratio is in the range of 1–30, and the pressure in the top of the column (absolute pressure) is in the range of 10–60 kPa. Incidentally, the step for the removal of the high-boiling substances by the use of the high-boiling separating column (60) and the step for the removal of the azeotropic solvent by the use of the solvent separating column (70) may be both carried out sequentially in either order.

The deposition of a gel-like substance on the inner wall and the bottom of the column for azeotropic dehydration (40) has occurred heretofore. Specifically, the deposition takes place on the inner wall and the stepped plates of the column for azeotropic dehydration or on the pits in the stepped plate members. Moreover, since the deposited substance is not easily removed by washing with water, the column for azeotropic dehydration and the peripheral appliances have required a periodic cleaning with an alkali, for example, at the plant for the production of maleic anhydride. This invention, however, by using a hydrophilic azeotropic solvent is enabled to repress the deposition of a gal-like substance originating in impurities and the generation of a blocking substance owing to the precipitation of maleic acid and fumaric acid and consequently accomplish the protracted operation of the plant.

This invention may obtain the maleic anhydride (81) as a finished product by causing the maleic anhydride stripped of the azeotropic solvent as described above and stripped of the high-boiling substance as well to be further supplied to the purifying column (80) and purified therein. As regards the conditions for purification in the purifying column (80), it is proper to set the absolute pressure in the top of the column in the range of 2–40 kPa and the temperature of the top of the column in the range of 80–170° C. The other conditions heretofore known to the art are usable.

The second aspect of this invention concerns a method for producing maleic anhydride comprising an azeotropic distillation step to dehydrite a crude maleic acid-containing aqueous solution, which method is characterized by using as an azeotropic solvent a mixture of an azeotropic solvent (1) forming an azeotropic composition with water and exhibiting a maximum dissolving concentration in water in the range of 0.1–5% by weight at a temperature of 20° C. and an azeotropic solvent (2) forming an azeotropic composition with formic acid and/or acetic acid.

When an organic solvent having a low degree of solubility in water is used in the azeotropic dehydration of the crude maleic acid-containing aqueous solution, since this organic solvent has low or no solubility in with water and maleic acid at the internal temperature of the distilling column, the water and the azeotropic solvent contained in the crude maleic acid-containing aqueous solution assume the state of oil-water separation within the distilling column. The maleic acid and the aldehyde and the quinone, i.e. impurities, which are contained in the crude maleic acid-containing aqueous solution are soluble in water and are present mainly in the water phase. Thus, they are concentrated in the water phase, disposed to promote the reaction of condensation of the aldehyde and the quinone, and compelled to form one cause for yielding a solid precipitate. Further, since maleic acid and fumaric acid which is an isomer thereof and maleic acid and a maleic anhydride polymer are soluble in water have virtually no solubility in organic solvents, they tend to precipitate in an organic solvent, they likewise form one cause for blockage. In contrast, it has been found that when the azeotropic dehydration is carried out by using an organic solvent possessing hydrophilicity, the state of oil-water separation in the distilling column is alleviated, the localization of an aldehyde and a quinone into the water phase is repressed, the concentrations of these compounds in the water phase are lowered, and the reaction of condensation by these two compounds is controlled. As the organic solvent possessing such hydrophilicity, this invention has decided to use an azeotropic solvent (1) which exhibits a maximum dissolving concentration in water in the range of 0.1–5% by weight at a temperature of 20° C. and therefore forms an azeotropic composition with water. The azeotropic solvent (1) indeed forms an azeotropic composition with water but is difficult to form an azeotropic composition with such light boiling acid components as are by-produced during the course of the reaction of maleic anhydride, particularly formic acid and/or acetic acid which are main components thereof. Thus, the azeotropic dehydration encounters difficulty in removing formic acid and/or acetic acid. Further, since formic acid and/or acetic acid do not form an azeotropic composition with water, the expulsion of water by distillation does not expel formic acid and/or acetic acid azeotropically with water. This invention, therefore, in case of need to expel formic acid and/or acetic acid by azeotropi distillation has elected combined use of an azeotropic solvent (1) and an azeotropic solvent (2) capable of forming an azeotropic composition with formic acid and/or acetic acid with the object of preventing the formation of a blocking substance during the course of the azeotropic dehydration and azeotropically removing the light boiling acid components by-produced during the course of the reaction. Incidentally, the term "light boiling acid components" as used in the present specification refers to compounds of such acids possessing lower boiling points than maleic acid as formic acid, acetic acid, and acrylic acid.

The azeotropic solvent (1) to be used in this invention is an organic solvent which exhibits a maximum dissolving concentration in water in the range of 0.1–5% by weight, preferably in the range of 0.5–4% by weight, and particularly preferably in the range of 1–3% by weight. If the maximum dissolving concentration in water falls short of 0.1% by weight, the shortage will tend to induce the state of oil-water separation mentioned above. Conversely, if the maximum dissolving concentration exceeds 5% by weight, though the excess will bring the effect of improving the state of oil-water separation, it will be at a disadvantage, when the organic solvent distilled through the top of the column together with water by the azeotropic dehydration is cooled and then separated from the water and recovered for reuse, in increasing the loss of the organic solvent into the water phase and decreasing the quantity of the organic solvent separated and recovered.

Further, the azeotropic solvent (1) to be used in this invention is preferred to exhibit the maximum dissolving concentration of maleic acid in the azeotropic solvent (1) in the range of 0.1–10.0% by weight, preferably 0.1–8.0% by weight, and particularly preferably 0.3–7.0% by weight, more particularly preferably 1.0–7.0% by weight at a temperature of 20° C. (under normal pressure). The reason for this maximum dissolving concentration is that when the aforementioned organic solvent to be used in this invention exhibits a high maximum dissolving concentration in maleic acid and possesses affinity for maleic acid, it is capable of preventing the precipitation of a water-soluble solid substances such as maleic acid, fumaric acid, and a maleic anhydride polymer during the course of the azeotropic dehydration and, at the same time, preventing the isomerization of maleic acid into fumaric acid and the precipitation of fumaric acid.

The azeotropic solvent (1) to be used in this invention is preferred to have a boiling point in the range of 80–190° C., preferably in the range of 100–170° C., and particularly preferably in the range of 110–160° C. If the boiling point exceeds 190° C., the excess will be at a disadvantage in suffering the boiling point to approximate closely to the boiling point of maleic anhydride and heightening the proportion at which the maleic anhydride is expelled by distillation together with the azeotropic solvent. Then, if the boiling point falls short of 80° C., the shortage will be at a disadvantage in lowering the temperature of the reaction of dehydration in the distilling column and lowering the speed of dehydration possibly to the extent of preventing the production from proceeding advantageously.

As the azeotropic solvent (1) to be used in this invention, the azeotropic solvent (1) described in the first aspect of this invention can be used. Specifically, the organic solvents described in the first aspect of this invention are ketones such as MIBK, diisopropyl ketone, 3-pentanone, 2-hexanone, 3-hexanone, and 2-heptanone, esters such as amyl acetate and allyl acetate, and alcohols such as methyl cyclohexanol and 2-ethyl-1-hexanol. This invention particularly prefers to use such ketones as MIBK, diisopropyl ketone, and 2-hexanone and such esters as allyl acetate. The reason for this choice is that such ketones and esters possess solubility in water, heighten the degrees of solubility of maleic acid, fumaric acid, and maleic acid and maleic anhydrice polymer in the azeotropic solvent, and allow solution of the problem of precipitation. Particularly, ketones prove preferable since they excel in the ability to solve maleic acid. The reason for the choice of ketones is that they satisfy the conditions mentioned above, excel in the effect to prevent the occurrence of a blocking substance during the course of the production of maleic anhydride and in the solubility, and exhibit no reactivity with maleic acid and maleic anhydride which are the target products. This invention can use the azeotropic solvents (1) mentioned above either singly or in the form of a combination of two or more members.

As the azeotropic solvent (2) to be used in this invention, a wide variety of azeotropic solvents which are capable of forming an azeotropic composition with formic acid and/or acetic acid are usable. More specifically, hydrocarbons such as toluene, xylene, octane, cumene, mesithylene, ethyl benzene, and dimethyl cyclohexane, sulfonates such as isopropyl sulfide and allyl sulfide, and halogenides such as bromobenzene and iodo propane can be used advantageously. The boiling points of these compounds, the points of azeotrope thereof with formic acid, and the points of azeotrope thereof with acetic acid are shown in Table 1.

The azeotropic solvent (2) to be used in this invention is preferred to have a boiling point in the range of 80–190° C., preferably in the range of 100–170° C., and particularly preferably in the range of 110–160° C. under a pressure of 1013 hPa. If the boiling point exceeds 190° C., the excess will be at a disadvantage in suffering this temperature to approximate closely to the boiling point of maleic anhydride and heightening the proportion in which the maleic anhydride is expelled by distillation together with the azeotropic solvent. Conversely, if this boiling point falls short of 80° C., the shortage will be at a disadvantage in lowering the temperature of the reaction of dehydration in the distillating column and lowering the speed of dehydration and preventing the production from proceeding advantageously. This invention allows the azeotropic solvents (2) mentioned above to be used either singly or in the form of a combination of two or more members.

Further, in the azeotropic solvents (2) enumerated above, the hydrocarbons can be used particularly favorably since they are easy to procure as general-purpose articles and are stable in a wide range of working temperatures.

TABLE 1

| Azeotropic solvent (2) | Boiling point (° C.) | Point of azeotropy with (° C.) | |
| --- | --- | --- | --- |
| | | Formic acid | Acetic acid |
| Toluene | 110.7 | 85.8 | 100.6 |
| o-Xylene | 143.6 | 95.5 | 116.0 |
| n-Octane | 125.8 | 90.5 | 105.1 |
| Cumene | 152.3 | 97.2 | 116.8 |
| Ethyl benzene | 136.2 | 94.0 | 114.7 |
| 1,3-dimethyl cyclohexane | 120.7 | 89.0 | 109.0 |
| Isopropyl sulfide | 120.5 | 93.5 | 111.5 |
| Allyl sulfide | 139.4 | 97.5 | 116.6 |
| Promobenzene | 156.1 | 98.1 | 118.4 |
| 1-Iodo propane | 102.4 | 82 | 99.2 |

In this invention, as mentioned above, it is preferable to contemplate using the mixture of the azeotropic solvent (1) and the azeotropic solvent (2) with the object of preventing the occurrence of a blocking substance and removing formic acid and acetic acid by means of azeotropy as well. In this case, the mixing ratio of the two azeotropic solvents is preferred to be such that the proportion of the azeotropic solvent (2) to be contained may be in the range of 1–40% by weight, preferably in the range of 3–35% by weight, and particularly preferably in the range of 5–30% by weight, based on the total weight of the mixture of the azeotropic solvent (1) and the azeotropic solvent (2). By setting the mixing ratio at a level exceeding 1% by weight, it is made possible to exalt the efficiency of removal of light boiling acid components such as formic acid and acetic acid which are by-produced. Conversely, by setting the mixing ratio at a level falling short of 40% by weight, it is made possible to remove the light boiling acid components without conspicuously lowering the effect of the use of a hydrophilic organic solvent manifested in the repression of precipitation and is enable to perform purification by the distillation for azeotropic dehydration to proceed effectively.

As concrete examples of the mixture of azeotropic solvents, the combination of 95% by weight of MIBK as the azeotropic solvent (1) and 5% by weight of o-xylene as the azeotropic solvent (mixture A), the combination of 80% by weight of MIBK as the azeotrotpic solvent (1) and 20% by weight of n-octane as the azeotropic solvent (2) (mixture B), and the combination of 75% by weight of 2-hexanone as the azeotropic solvent (1) and 25% by weight of ethyl benzene as the azeotropic solvent (2) (mixture C) may be cited. When the mixture A, for example, is used as the azeotropic solvent, the distillate composition exhibits a point of azeotropy of 88.2° C. with water and forms a ternary solvent mixture exhibiting a point of azeotropy of 95.5° C. with formic acid. When a plate column using 5 plates in the concentrating part and 10 plates in the recovering part is adopted as the azeotropic distilling column and operated with the temperature of the bottom of the column set at 170° C., the resultant azeotropic composition is formed of 20.1% by weight of the waster phase and 79.9% by weight of the oil phase of the mixture A. By adopting the method described above, it is made possible, when the column incurs blockage owing to the complication of the internal structure thereof, to prevent the deposition of a blocking substance in the distilling column for azeotropic dehydration demanding an irksome and difficult washing work and allow such light boiling acid components such as formic acid to be removed simply. The mixture of azeotropic solvent (1) with azeotropic solvent (2) in this invention is required to exhibit a maximum dissolving concentration of maleic acid in azeotropic solvent (1) in the range of 0.1–10.0% by weight, preferably 0.1–8.0% by weight, and particularly preferably 0.3–7.0% by weight, more particularly preferably 1.0–7.0% by weight, at a temperature of 20° C. (under normal pressure), and at the same time exhibites a maximum dissolving concentration of the mixture in water in the range of 0.1–5% by weight, preferably in the range of 0.5–4% by weight, and particularly preferably in the range of 1–3% by weight, at a temperature of 20° C.

The aforementioned mixture of the azeotropic solvents (1) and (2), when used in the production of maleic anhydride particularly by the catalytic gas phase oxidation of benzene, is effective since the aldehyde and the quinone which are causative substances for a condensate are by-produced in large quantities. These causative substances for a blocking substance, however, are generated not only when benzene is used as the raw material but also when the maleic anhydride is formed as a by-product in the production of phthalic anhydride using such an aliphatic hydrocarbon as n-butane, or naphthalene, or o-xylene as the raw material. The method contemplated by this invention, therefore, is useful in the method of production using any of the conceivable raw materials. It is effective also when the method of production incorporates a step which comprises absorbing by washing with water the maleic anhydride-containing gas obtained by the reaction of catalytic gas phase oxidation of n-butane, for example, and subjecting the collected gas to the distillation for azeotropic dehydration using an organic solvent possessing the characteristic properties mentioned above. The method of this invention, by manifesting an effect in preventing the column for azeotropic dehydration from being blocked and attaining effective removal of such light boiling acid components as formic acid, is enabled to afford the column a protracted operation.

The quantity of the mixture of such azeotropic solvents (1) and (2) to be used in the process for azeotropic dehydration is preferred to be in the range of 0.5–10 parts by weight, particularly in the range of 2–5 parts by weight, based on the total of the water contained in the crude maleic acid-containing aqueous solution and the water generated by the anhydridization taken as one part by weight, though variable with the percentage composition of the organic solvent or the solvent mixture to be used. When the quantity of the organic solvent to be used per unit quantity of water is small, the quantity of heat to be consumed will become so small as to render the production economically advantageous.

Now, one example of the preferred embodiment of the method for the production of maleic anhydride according to this invention will be described below with reference to FIG. 1.

First, the second aspect of this invention can be implemented by following the first aspect of this invention described above with modifications. So, the differences between the first and the second aspect of the invention will be explained. The present invention is characterized by using the mixture of the azeotropic solvent (1) and the azeotropic solvent (2) as the azeotropic solvent in the dehydration of a crude maleic acid-containing aqueous solution by azeotropic distillation. For the mixture, the various organic solvents mentioned above are usable. It is particularly preferable to use MIBK as the azeotropic solvent (1) and it is preferable to use xylene or octane as the azeotropic solvent (2). The conditions for the azeotropic dehydration are variable with the kind of azeotropic solvent. When the mixture of 75% by weight of MIBK and 25% by weight of xylene is used as the azeotropic solvent, for example, 2.2–3.8 parts by weight of MIBK and 0.8–1.2 parts by weight of o-xylene are supplied in a total of 3–5 parts by weight per one part by weight of the crude maleic acid-containing aqueous solution to the column for azeotropic dehydration (40). The MIBK and the toluene may be mixed advance and supplied in the form of a mixture to the column for azeotropic dehydration (40) or they may be separately supplied thereto. The pressure (absolute pressure) in the top of the column is generally in the range of 100–2000 hPa and preferably in the range of 300–1500 hPa. If the pressure falls short of 100 hPa, the shortage will be at a disadvantage in unduly enlarging the vacuum device, lowering the internal temperature of the column, and crystallizing maleic acid and fumaric acid possibly to the extent of defying distillation. Conversely, if this pressure exceeds 2000 hPa, the excess will be at a disadvantage in not only heightening the temperature of the bottom of the column and compelling the boiler to gain in size and tend to generate a polymer but also requiring the equipment to be proofed against pressure and rendering the production uneconomical. Then, the temperature of the top of the column is in the range of 50–150° C., preferably in the range of 60–130° C. If this temperature falls short of 50° C., the shortage will result in suffering the capacitor to gain in size unduly. Conversely, if the temperature exceeds 150° C., the excess will be at a disadvantage in not only entailing an unduly large addition to the size of the capacitor but also increasing the distillation of maleic anhydride to the top of the column and aggravating the loss of the maleic anhydride.

The temperature of the bottom of the column is in the range of 130–200° C. and preferably in the range of 150–195° C. If this temperature falls short of 130° C., the shortage will be at a disadvantage in retarding the reaction of dehydration of maleic acid, preventing the maleic acid from being sufficiently dehydrated, and eventually degrading the yield of maleic anhydride. Conversely, if the temperature exceeds 200° C., the excess will be at a disadvantage in suffering this temperature to approximate closely to the boiling point of maleic anhydride and inducing the phenomenon of diffusion and accelerating the occurrence of decomposition and polymerization. For the purpose of establishing such conditions for the azeotropic dehydration, it suffices to adjust such factors as the kind and the quantity of addition of the azeotropic solvent, the concentration of water in the crude maleic acid-containing aqueous solution, the alteration of the number of steps of supply of the raw material, the ref lux ratio of the cooling device to be annexed to the top of the column, the number of plates in the column, the temperature, the pressure, and others.

As the azeotropic solvent to be used in the azeotropic dehydration, the azeotropic solvent (71) which has been recovered in the process for producing maleic anhydride may be reused. The azeotropic solvent does not need to be directly supplied to the column for azeotropic dehydration (40) as illustrated in FIG. 1 but may be supplied into the column for azeotropic dehydration (40) as mixed with the raw material being supplied.

The present invention likewise prefers to annex the oil-water separating column (50) to the top of the column for azeotropic dehydration (40) and refluxes the azeotropic solvent in the distillate from the top of the column during the course of the azeotropic dehydration. In this invention, the crude maleic anhydride (11) may be supplied together with the bottom liquid of the column for azeotropic dehydration (4) to the high boiling separating column (60) and purified therein as illustrated in FIG. 1.

Incidentally, the step for the removal of the high-boiling substances by the use of the high-boiling separating column (60) and the step for the removal of the azeotropic solvent by the use of the solvent separating column (70) may be both carried out sequentially in either order.

The deposition of a gel-like substance on the inner wall and the bottom of the column for azeotropic dehydration (40) has occurred heretofore. Specifically, the deposition takes place on the inner wall and the stepped plates of the column for azeotropic dehydration or on the pits in the stepped plate members. Moreover, since the deposited substance is not easily removed by washing with water, the column for azeotropic dehydration and the peripheral appliances have required a periodic cleaning with an alkali, for example, at the plant for the production of maleic anhydride. This invention, however, is enabled by using the mixture of a hydrophilic azeotropic solvent and an organic solvent capable of forming an azeotropic composition with formic acid and/or acetic acid to repress the deposition of a gel-like substance originating in impurities and the generation of a blocking substance owing to the precipitation of maleic acid and fumaric acid and consequently accomplish the protracted operation of the plant and effect the removal of the by-produced acid components during the process for azeotropic dehydration by distillation as well.

Also in the present invention, the maleic anhydride which has been deprived of the azeotropic solvent in the manner described above and further deprived of the high boiling substances may be supplied to the purifying column (80) and purified therein so as to reduce the maleic anhydride (81) to a finished product.

Embodiments

Now, this invention will be described more specifically below with reference to working examples thereof.

<Referential Example 1: Method for Selection of Solvent by Maximum Dissolving Concentration of Organic Solvent in Water>

One species of organic solvent or a mixture of two or more species of solvent to be used in this invention was selected by the following method. In a tightly closable glass vessel measuring 100 ml in inner volume and furnished with a lid, 80 g of purified water kept at a temperature of 20° C. was placed and stirred with a stirrer and meanwhile a given organic solvent or solvent mixture was added dropwise to the stirred water. The state of solution consequently assumed after one hour's standing was visually observed. When any residue of the solute was found in the solution, the confirmation of the solubility mentioned above was repeated, with the quantity of dropwise addition per round decreased. The minimum quantity of the organic solvent or the solvent mixture as the solute to be used for the dropwise addition was set at 0.02 g. In this manner, the maximum quantity of dropwise addition (weight of solute) which was found to give no residue of solute was found and reduced to the maximum dissolving concentration in 80 g of water (solvent). Specifically, the magnitude found by the following formula, Maximum dissolving concentration (% by weight)={Solute/(Solute+Solvent)}×100 is the maximum dissolving concentration contemplated by this invention. The numerical values thus obtained almost agreed with the data on the solubility of the relevant solvent in water inserted in the chemical handbook mentioned in the text and in Beilstein. The present example concerns computation of the maximum dissolving concentration of a given solute in 80 g of a solvent in accordance with the formula mentioned above. The maximum dissolving concentration was determined at a solution temperature of 20° C. Incidentally, when two or more species of organic solvent are mixed and used in the distillation for azeotropic dehydration, the maximum dissolving concentration of the mixture is determined by the method described above.

The data of solubility obtained of o-xylene, methyl isobutylketone (MIBK), diisopropylketone (DIPD), diisobutyl ketone (DIBK), dibutyl ether (DBE), and a solvent mixture formed of 85% of MIBK and 15% of o-xylene and evaluated by the method described above are shown in Table 2.

<Referential Example 2: Determination of Maximum Dissolving Concentration of Maleic Acid or Fumaric Acid in the Solvent>

In a tightly closable glass vessel measuring 100 ml in inner volume and furnished with a lid, 80 g of a given solvent kept at a temperature of 20° C. was placed and stirred with a stirrer and meanwhile maleic acid or fumaric acid of the special reagent grade as defined in the paragraph covering the determination of maximum dissolution concentration was added to the stirred solvent. The state of solution consequently assumed was visually confirmed. When the solute left any residue behind in the solution even after one hour's stirring, the sample was reported as insoluble. When the residue of the solute was found, the confirmation of the maximum dissolving concentration mentioned above was repeated, with the quantity of addition per round decreased. The minimum quantity of addition was set at 0.01 g. Thus, the maximum quantity of dropwise addition (weight of solute) which was recognized to have given rise to no residue of elute was determined and computed as the maximum dissolution concentration in 80 g of a given solvent. Specifically, the magnitude found by the following formula, Maximum dissolving concentration (% by weight)={Solute/(Solute+Solvent)}×100 is the maximum dissolving concentration contemplated by this invention. When the elute left any residue behind in the solution even at the minimum quantity of dropwise addition of 0.01 g (0.006% by weight), the sample was reported as insoluble. Incidentally, the maximum dissolution concentration was measured at a solution temperature of 20° C.

The results were as shown in Table 2. It is noted from Table 2 that the maximum dissolution concentration in water and the maximum dissolution concentration of maleic acid or fumaric acid had relatively higher magnitudes for MIBK than for other substances. DIPD, DIBK, and ketone group showed inclinations toward lowering the maximum dissolution concentration to levels below that of MIBK which was observed to dissolve maleic acid and fumaric acid. The o-xylene, however, did not dissolve maleic acid or fumaric acid and showed virtually no maximum dissolving concentration of these substances in water. While the o-xylene exhibited low solubility in water and failed to dissolve maleic acid or fumaric acid, the solvent mixture formed of 85% of MIBK and 15% of o-xylene exhibited a relatively high maximum dissolving concentration of 1.57 in water. The maximum dissolving concentration of maleic acid was 3.41 and the maximum dissolving concentration of furamic acid was 0.11, i.e. the levels higher than the maximum dissolving concentrations of other substances.

TABLE 2

| Determination | Maximum dissolving concentration in | Maximum dissolving concentration in solvent (% by weight) | |
|---|---|---|---|
| Solvent | water (% by weight) | Maleic acid | Fumaric acid |
| o-Xylene | 0.02 | Insoluble | Insoluble |
| MIBK | 1.85 | 4.14 | 0.14 |
| DIPK | 0.41 | 1.22 | 0.02 |
| DIBK | 0.05 | 0.62 | Insoluble |
| DBE | 0.03 | 0.34 | Insoluble |
| MIBK 85% + o-Xylene 15% | 1.57 | 3.41 | 0.11 |

EXAMPLE 1

In a vessel formed by fitting a stirrer and a reflux condenser to a 1-liter glass flask, a liquid composition assumed to fill a distilling column for azeotropic dehydration was prepared by adding to 500 g of a liquid composed of 82% by weight of a varying organic solvent shown in Table 3, 12% by weight of maleic acid, and 6% by weight of purified water 9000 ppm by weight of formaldehyde, 150 ppm by weight of benzoquinone, and 150 ppm by weight of hydroquinone based on the quantity of maleic acid. The liquid composition was heated in an oil bath under normal pressure to determine the occurrence of a condensate as a precipitated substance.

The conditions of the experiment included the temperature: the inner temperature of 100° C. or the temperature required by a liquid sample in assuming the state of boiling, the time for testing the thermal aging: two hours (the time elapsing after arrival of the inner temperature at 95° C.), and the confirmation of the formation of a condensate: the procedure comprising the steps of cooling a sample, then filtering the cooled sample with a membrane filter 1 µm in thickness under reduced pressure, and visually examining the membrane filter to determine whether it had formed on the surface thereof a deposit of a solid condensate as a precipitate. The results were as shown in Table 3. Incidentally, the state of oil-water separation during the application of heat after the test time as indicated in the table represents the outcome of the observation of the state of a sample immediately after two hours' thermal aging test.

From the results of Table 3, it is noted that when MIBK and a solvent mixture composed of 85% of MIBK and 15% of o-xylene were used each as an azeotropic solvent, the respective compositions assumed to be formed in the column were each in a homogeneous state revealing no discernible oil-water separation. This homogeneous state may be logically explained by a supposition that the MIBK and the solvent mixture composed of 85% of MIBK and 25% of o-xylene exhibited high maximum dissolving concentration of the solvent mixture in water and also possessed solubility of acid components such as maleic acid and fumaric acid in the solvent mixture. When DBE and o-xylene were used, however, the respective sample liquids each underwent oil-water separation and consequently assumed the state of separation into two phases. As respects the formation of a condensate, when the MIBK solvent was used, the membrane filter after passing the relevant sample liquid failed to obtain any solid deposit of a condensate on the surface thereof. In contrast, when the DBE solvent and the o-xylene solvent were used, the formation of a condensate was confirmed by the detection of a solid deposit on the membrane filter.

TABLE 3

| Organic solvent in sample liquid | MIBK | DBE | o-Xylene | MIBK 85%, o-Xylene 15% |
|---|---|---|---|---|
| State of oil-water separation during application of heat after test time | No | Yes | Yes | No |
| Confirmation of formation of condensate | No | Yes | Yes | No |

EXAMPLE 2

Maleic anhydride was produced by following the procedure illustrated in FIG. 1.

First, a maleic anhydride-containing reaction gas discharged from the site of a reaction of catalytic gas phase oxidation of benzene was introduced into a maleic anhydride collecting device (10) the outlet gas temperature of which was controlled to 60° C. to collect the maleic anhydride. Then, the outlet gas of this maleic anhydride collecting device (10) was introduced into a water-washing absorbing column (20). Subsequently, the gas was washed with water in the water-washing absorbing column (20) to obtain an aqueous solution containing 42% by weight of crude maleic acid. The crude maleic acid-containing aqueous solution consequently obtained was found to contain therein 3200 ppm by weight of formaldehyde, 57 ppm by weight of benzoquinone, and 30 ppm by weight of hydroquinone. This crude maleic acid-containing aqueous solution was subjected to azeotropic dehydration using MIBK as an azeotropic dehydration solvent.

A distilling column using five plates 32 mm in diameter in the concentrating part and ten plates 50 mm in diameter in the recovering part was used as a column for azeotropic dehydration (40). An azeotropic solvent was supplied to the column through the top thereof in a quantity 3.5 times the total weight of the dissolving water of the aqueous maleic acid solution and the water formed by the relevant reaction and was used to effect azeotropic dehydration for 8 hours under normal pressure at a column bottom temperature of 170° C. At the time that the composition in the system was stabilized, the bottom liquid of the column was composed of 90.2% by weight of maleic anhydride, 7.5% by weight of MIBK, 2.24% by weight of maleic acid, 0.06% by weight of phthalic anhydride, not more than 0.01% by weight of formaldehyde, not more than 0.01% by weight of benzoquinone, and 0.01% by weight of hydroquinone and the distillate from the top of the column was composed of 78% by weight of MIBK phase and 22% by weight of water phase. The formaldehyde and the maleic acid were nearly wholly distributed in the water phase and respectively accounted for 0.51% by weight and 0.0001% by weight. After eight hours' operation, the interior of the column showed no discernible sign of defilement with the condensates of aldehydes and quinones or with the deposits thereof. No sign of clogging with the deposit of fumaric acid was detected, either. The results were as shown in Table 4. In the observation of "the state of defilement in the column" indicated in Table 4, the condensate and the maleic anhydride polymer were discriminated as follows. The sticking substance which could be removed from the distilling column by washing with cold water or hot water after the operation of distillation was the maleic anhydride polymer. The black deposit which could not be removed by this treatment and was required to be removed by solution with a 0.1N dilute aqueous sodium hydroxide solution was rated as the condensate.

COMPARATIVE EXAMPLE 1

The distillation for azeotropic dehydration was performed for 8 hours at the same bottom temperature as in Example 2 by following the procedure of Example 2 while using o-xylene in the place of the azeotropic solvent MIBK and supplying the azeotropic solvent to the column through the top thereof in a quantity 2.5 times the total weight of the dissolving water in the aqueous maleic acid solution and the water formed by the relevant reaction. The results were as shown in Table 4.

TABLE 4

| Azeotropic solvent Item of determination | Example 2 MIBK | Comparative Example 1 o-Xylene |
|---|---|---|
| Composition of distilled oil phase | | |
| Water (% by weight) | 2.06 | 0.02 |
| Formaldehyde (% by weight) | 0.01 | 0.01 |
| Composition of distilled water phase | | |
| Azeotropic solvent (% by weight) | 1.63 | 0.02 |
| Formaldehyde (% by weight) | 0.51 | 0.50 |
| Composition and yield of bottom liquid | | |
| Maleic acid (% by weight) | 2.2 | 1.5 |
| Fumaric acid (% by weight) | 1.6 | 1.7 |
| Ratio of conversion of maleic acid (%) | 97.5 | 98.5 |
| Ratio of selectivity of fumaric acid (%) | 1.6 | 1.6 |
| State of defilement of the interior of column | | |
| Presence or absence of condensate | None | Copious presence |
| Presence or absence o maleic anhydride polymer | None | Slight presence |
| Precipitation of fumaric acid | None | Slight presence |

It is clear from Table 4 that after 8 hours' operation of distillation, the interior of the column for azeoropic dehydration was observed to be defiled with the condensate as a blocking substance, the deposit of maleic acid, and the deposit of a maleic acid polymer. When MIBK was used as a solvent for azeotropic dehydration, the interior of the column showed absolutely no sign of defilement with the condensate and the maleic acid polymer and with the deposit. It showed no discernible sign of the blocking with the deposit of fumaric acid. The operation of distillation, therefore, could be continued for a long time exceeding 8 hours. When o-xylene was used as a solvent for azeotropic dehydration by way of comparison, copious deposit of the condensate was observed. Further, the precipitation of fumaric acid was observed and the deposit thereof in the form of crystals was detected particularly on the trays in the recovering part of the distilling column.

COMPARATIVE EXAMPLE 2

The distillation for azeotropic dehydration was performed for 8 hours at the same bottom temperature as in Example 2 by following the procedure of Example 2 while using DBE in the place of the azeotropic solvent MIBK and supplying the azeotropic solvent to the column through the top thereof in a quantity 4.0 times the total weight of the dissolving water in the aqueous maleic acid solution and the water formed by the relevant reaction. As a result, the interior of the column was found to be defiled in the same manner as in Comparative Example 1. The results were as shown in Table 5.

COMPARATIVE EXAMPLE 3

The distillation for azeotropic dehydration was performed for 8 hours at the same bottom temperature as in Example 2 by following the procedure of Example 2 while using DIBK in the place of the azeotropic solvent MIBK and supplying the azeotropic solvent to the column through the top thereof in a quantity 1.5 times the total weight of the dissolving water in the aqueous maleic acid solution and the water formed by the relevant reaction. As a result, the interior of the column was found to be defiled in the same manner as in Comparative Example 1. The results were as shown in Table 5. Incidentally, the evaluation of "the state of defilement in the column" indicated in Table 5 was based on the same standard as used in Table 4.

TABLE 5

| Azeotropic solvent Item | Comparative Example 2 DBE | Comparative Example 3 DIBK |
|---|---|---|
| State of defilement in the column | | |
| Presence or absence of condensate | Copious presence | Copious presence |
| Presence or absence of maleic anhydride polymer | Slight presence | Slight presence |
| Deposition of fumaric acid | Slight presence | Slight presence |

(1) The organic solvent such as MIBK and acetic acid were tested by the gas chromatography using a column made by J & W scientific Corp. and sold under the product code of "DB-5."

(2) Formic acid, maleic acid, and fumaric acid were tested by the liquid chromatography using a column made by GL Science Corp. and sold under the trademark designation of "Inertsil ODS-3."

EXAMPLE 3

Maleic anhydride was produced by following the procedure illustrated in FIG. 1.

First, a maleic anhydride-containing reaction gas discharged from the site of a reaction of catalytic gas phase oxidation of benzene was introduced into a maleic anhydride collecting device (10) the outlet gas temperature of which was controlled to 60° C. to collect crude maleic anhydride (11). Then, the outlet gas of this maleic anhydride collecting device (10) was introduced into a water-washing absorbing column (20). Subsequently, the gas was washed with water by the water-washing absorbing column (20) to obtain an aqueous crude maleic acid containing solution. The solution was found to contain therein 42% by weight of maleic acid, 58% by weight of water, 2000 ppm by weight of acetic acid, and 70 ppm by weight of formic acid. This crude maleic acid-containing aqueous solution was subjected to azeotropic dehydration using a mixture composed of 85% by weight of MIBK and 15% by weight of o-xylene.

A distilling column using five plates 32 mm in diameter in the concentrating part and ten plates 50 mm in diameter in the recovering part was used as a column for azeotropic dehydration (40). An aqueous crude maleic acid-containing solution was supplied through the 10th plate as reckoned from the bottom of the column. The azeotropic solvent was supplied to the column through the top thereof in a quantity 3.5 times the total weight of the dissolving water in the aqueous maleic acid solution and the water formed by the relevant reaction and was used to effect azeotropic dehydration for 8 hours under normal pressure at a column bottom temperature of 170° C. At the time that the composition in the system was stabilized, the bottom liquid of the column was composed of 88.41% by weight of maleic anhydride, 0.04% by weight of MIBK, 8.70% by weight of o-xylene, 1.81% by weight of maleic acid, 1.04% by weight of fumaric acid, 0 ppm by weight of formic acid, and 0 ppm by weight of acetic acid, which fact indicates that the presence in the bottom liquid of the column of by-produced acids, i.e. light boiling substances in the liquid supplied into the column for azeotropic dehydration, could be eliminated. After the operation, the interior of the column showed no discernible sign of defilement with the condensates of aldehydes and quinones or with the deposits thereof. No sign of clogging with the deposit of fumaric acid was detected, either. The evaluation of "the state of defilement in the column" as indicated in Table 6 was based on the same standard as in Table 4.

EXAMPLE 4

The distillation for azeotropic dehydration was performed for 8 hours under the same conditions as in Example 3 by following the procedure of Example 3 while forming the mixture of azeotropic solvents with 95% by weight of MIBK and 5% by weight of o-xylene. The results were as shown in Table 6. At the time that the composition in the system was stabilized, the acetic acid remained only in a minute quantity of 170 ppm by weight and the formic acid was absent as shown by the assay of 0 ppm by weight in the bottom liquid of the column. After the operation, the interior of the column showed no discernible sign of defilement with the condensates of aldehydes and quinones or with the deposits of the maleic anhydride polymer. No sign of clogging with the deposit of fumaric acid was detected, either. The evaluation of "the state of defilement in the column" as indicated in Table 6 was based on the same standard as in Table 4.

EXAMPLE 5

The distillation for azeotropic dehydration was performed for 8 hours under the same conditions as in Example 3 by following the procedure of Example 3 while forming the mixture of azeotropic solvents with 80% by weight of MIBK and 20% by weight of n-Octane and changing the column bottom temperature to 190° C. The results were as shown in Table 6. At the time that the composition in the system was stabilized, the acetic acid remained only in a quantity of 500 ppm by weight and the formic acid was absent as shown by the assay of 0 ppm by weight in the bottom liquid of the column. After the operation, the interior of the column showed no discernible sign of defilement with the condensates of aldehydes and quinones or with the deposits of the maleic anhydride polymer. No sign of clogging with the deposit of fumaric acid was detected, either.

EXAMPLE 6

The distillation for azeotropic dehydration was performed for 8 hours under the same conditions as in Example 4 by following the procedure of Example 3 while forming the azeotropic solvent with 100% by weight of MIBK. The results were as shown in Table 6. At the time that the composition in the system was stabilized, the acetic acid remained in a quantity of 2150 ppm by weight and the formic acid in a quantity of 100 ppm by weight in the composition of the bottom liquid of the column. That is, both acetic acid and formic acid were present in the bottom liquid of the column. After the operation, the interior of the column showed no discernible sign of defilement with the condensates of aldehydes and quinones or with the deposits of the maleic anhydride polymer. No sign of clogging with the deposit of fumaric acid was detected, either.

EXAMPLE 7

The distillation for azeotropic dehydration was performed for 8 hours under the same conditions as in Example 4 by following the procedure of Example 3 while forming the azeotropic solvent with 100% by weight of MIBK and changing the column bottom temperature to 190° C. The results were as shown in Table 6. At the time that the composition in the system was stabilized, the acetic acid remained in a quantity of 1720 ppm by weight and the formic acid in a quantity of 15 ppm by weight. Even when the column bottom temperature was raised from 170° C. to 190° C., both acetic acid and formic acid were present in the bottom liquid of the column. After the operation, the interior of the column showed no discernible sign of defilement with the condensates of aldehydes and quinones or with the deposits of the maleic anhydride polymer. No sign of clogging with the deposit of fumaric acid was detected, either.

TABLE 6

|  | Example 3 | Example 4 | Example 5 | Example 6 | Example 7 |
|---|---|---|---|---|---|
| Solvent for azeotropic dehydration | | | | | |
| Azeotropic solvent (1) | MIBK | MIBK | MIBK | MIBK | MIBK |
| Azeotropic solvent (2) | o-Xylene | o-Xylene | n-Octane | None | None |
| Mixing ratio of solvents (1) + (2) (% by wt.) | 85:15 | 95:5 | 80:20 | 100:0 | 100:0 |
| Bottom temperature of distilling column (° C.) | 170 | 190 | 190 | 170 | 190 |
| Composition of column bottom liquid | | | | | |
| Acetic acid (ppm) | 0 | 170 | 500 | 2150 | 1720 |
| Formic acid (ppm) | 0 | 0 | 0 | 100 | 15 |
| State of defile-ment in column | | | | | |
| Condensate | None | None | None | None | None |
| Maleic anhydride polymer | None | None | None | None | None |
| Deposition of fumaric acid | None | None | None | None | None |

What is claimed is:

1. A method for producing maleic anhydride comprising the step of azeotropic distillation of a crude maleic acid containing aqueous solution using one or more organic solvents selected from the group consisting of methyl isobutyl ketone, diisopropyl ketone, and 2-hexanone, wherein the crude maleic acid containing aqueous solution is obtained by washing with water a reaction gas produced by the catalytic gas phase oxidation of benzene.

2. A method for producing maleic anhydride comprising the step of azeotropic dehydration of a crude maleic acid containing aqueous solution is obtained by washing with water a reaction gas produced by the catalytic gas phase oxidation of benzene.

* * * * *